United States Patent
Barnhorst et al.

(10) Patent No.: US 6,489,496 B2
(45) Date of Patent: Dec. 3, 2002

(54) TRANSESTERIFICATION PROCESS

(75) Inventors: Jeffrey A. Barnhorst; Michael D. Staley; Dean A. Oester, all of Cincinnati, OH (US)

(73) Assignee: Cognis Corporation, Gulph Mills, PA (US)

( * ) Notice: Subject to any disclaimer, the term of this patent is extended or adjusted under 35 U.S.C. 154(b) by 11 days.

(21) Appl. No.: 09/891,573

(22) Filed: Jun. 26, 2001

(65) Prior Publication Data

US 2002/0028961 A1 Mar. 7, 2002

Related U.S. Application Data

(60) Provisional application No. 60/217,828, filed on Jul. 12, 2000, and provisional application No. 60/255,097, filed on Dec. 13, 2000.

(51) Int. Cl.$^7$ ............................................... C11C 1/00
(52) U.S. Cl. ...................... 554/169; 554/170; 554/172
(58) Field of Search ............................. 554/169, 170, 554/172

(56) References Cited

U.S. PATENT DOCUMENTS

| | | | |
|---|---|---|---|
| 2,474,006 A | | 6/1949 | Maycock |
| 5,399,731 A | * | 3/1995 | Wimmer .................... 554/167 |
| 5,762,800 A | | 6/1998 | Meikrantz et al. |
| 5,908,376 A | | 6/1999 | Macaluso et al. |

OTHER PUBLICATIONS

Liu et al., Journal of Agric. Food Chem., vol. 46, pp. 3835–3838, 1998.*

Noureddini, et al., "A Continuous Process for the Conversion of Vegetable Oils into Methyl Esters of Fatty Acids", JAOCS, vol. 75, No. 12, AOCS Press, (1998), pp. 1775–1783.

Gheorghiu, "A New Transesterification Technique for Oils and Fats—Fatty Acid Methyl Ester Production by Transesterification: a Continuous Non–Alkaline Catalytic Process", Oils–Fats–Lipids, Proceedings of the 21st World Congress of the International Society for Fat Research (ISF), The Hague, Oct. 1995, vol. 3, Published by PJ Barnes & Associates, (1996), pp. 489–496.

Noureddini, et al., "A Continuous Process For The Conversion Of Vegetable Oils into Biodiesel", Liq. Fuel Ind. Prod. Renewable Resour., Proc. Liq. Fuel Conf., 3rd (1996), pp. 83–88 & 90–94.

Choo, et al., "Conversion of Crude Palm Kernel Oil Into Its Methyl Esters on a Pilot Plant Scale", Palm Oil Research Institute of Malaysia (PORIM), Proc. –World Conf. Oleochem. (1991), pp. 292–295.

Costner Industries Nevada Corp. (CINC) Technical Bulletin for Liquid Centrifugal Processing, 1999.

* cited by examiner

Primary Examiner—Deborah D Carr
(74) Attorney, Agent, or Firm—John E. Drach

(57) ABSTRACT

The present invention pertains to a process for making an alkyl ester of a carboxylic acid via transesterification comprising the steps of: (1) reacting a carboxylic acid ester with an alcohol and an effective amount of a transesterification catalyst in a reaction zone to form a reaction mixture comprised of a product ester and a product alcohol; (2) passing the reaction mixture from step (1) through a centrifugal separation zone wherein the second alcohol is separated from the second ester. The process according to the invention allows for shorter reaction times and improved product yields.

12 Claims, 2 Drawing Sheets

TRANSESTERIFICATION PROCESS

CROSS-REFERENCE TO RELATED APPLICATIONS

This application claims the benefit of copending provisional application Ser. No. 60/217,828, filed on Jul. 12, 2000, and provisional application Ser. No. 60/255,097, filed on Dec. 13, 2000, the entire contents of each of which are incorporated herein by reference.

BACKGROUND OF THE INVENTION

The present invention relates to a process for making alkyl esters of carboxylic acids via transesterification wherein the product alcohol is removed from the reaction mixture rapidly and efficiently thereby enhancing the rate of the reaction and the overall yield of ester.

It is well known that the product composition of a transesterification reaction is governed by equilibrium thermodynamics. Thus, in order to realize the maximum amount of product ester, the product alcohol should be removed as rapidly as possible in order to displace the position of the equilibrium in favor of the products. However, in manufacturing scale operations, such product alcohol removal is not easily achieved. For example, in the batch transesterification of a triglyceride with methanol to form fatty acid methyl esters, a triglyceride, methanol and sodium methoxide are added together and reacted at 75–80° C. for one hour. The agitator is turned off and the mixture is allowed to settle. The glycerine layer will be on the bottom and is drained form the vessel. The agitator is turned on, additional sodium methoxide is added and the mixture is reacted for another hour at 75–80° C., glycerine drained, the crude methyl ester is water washed and dried. In a continuous process, the triglyceride, methanol and catalysts are metered together using pumps and mixing is accomplished by pumping the mixture through a static mixer and long lengths of piping to a settling tank. In this tank, the mixture is pumped in on one side of the tank, the methyl esters are removed on the other side and the glycerine is drained from the bottom. Once the methyl esters leave this settling tank, they are further mixed with additional methanol and catalyst, pumped through a static mixer, pushed through piping and into a second settling tank. The methyl esters are pumped from this tank and further refined.

The foregoing example shows that the removal of glycerine, the product alcohol in the transesterification of a triglyceide, is not normally achieved rapidly. Thus, the rate of the product methyl ester formation is not as great as could be achieved were the glycerine removed as its is formed. Rapid removal of glycerine would result in more favorable economics.

SUMMARY OF THE INVENTION

In its most general aspect, the present invention pertains to a process for making an alkyl ester of a carboxylic acid via transesterification comprising the steps of: (1) reacting a carboxylic acid ester with an alcohol and an effective amount of a transesterification catalyst in a reaction zone to form a reaction mixture comprised of a product ester and a product alcohol; (2) passing the reaction mixture from step (1) through a centrifugal separation zone wherein the second alcohol is separated from the second ester. The process according to the invention allows for shorter reaction times and improved product yields.

DETAILED DESCRIPTION OF THE INVENTION

Figure 1:
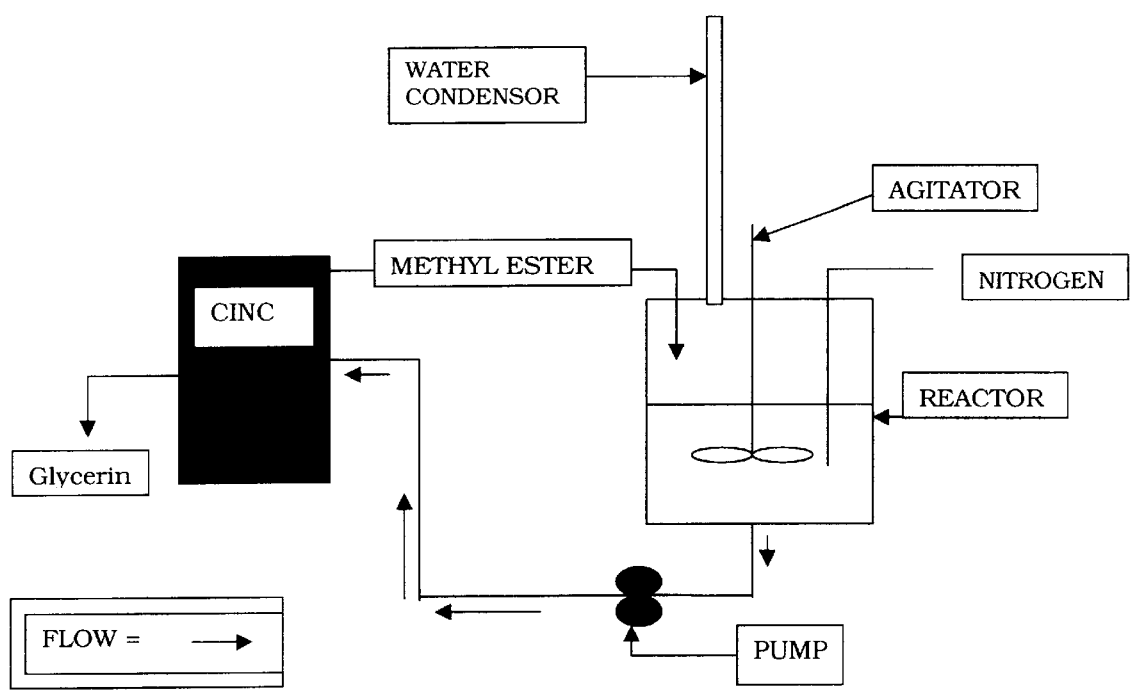
FIG. 1 is a flow diagram of the process according to the invention. The CINC is the centrifugal separator.
Figure 2:
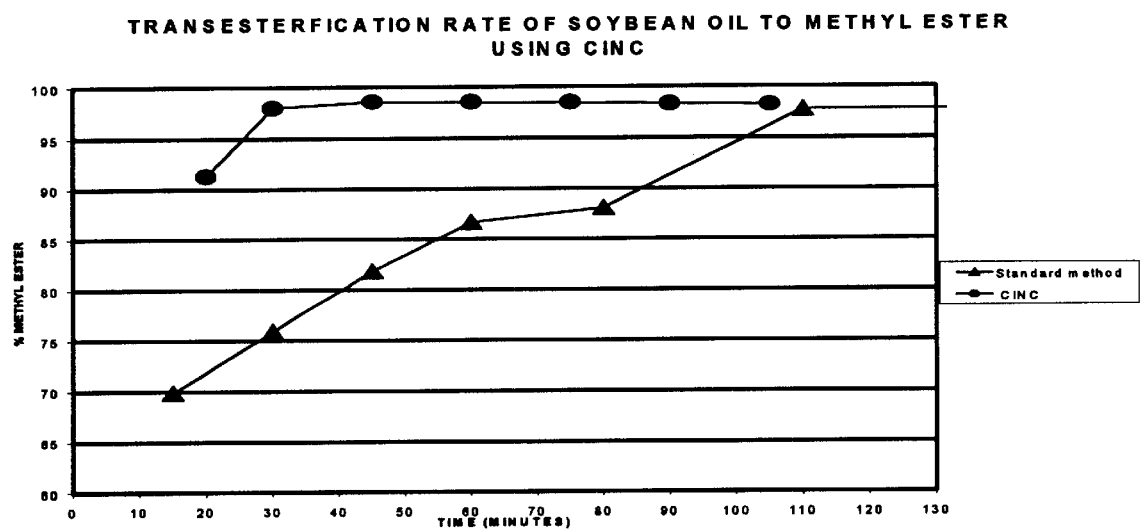
FIG. 2 is a graph showing the conversion rate of triglycerides to methyl esters versus time.

The process according to the invention is particularly applicable to transesterification reactions. Transesterification is well known to those skilled in the art and can be depicted by the following equation:

$RCOOR^1 + R^2OH \rightarrow RCOOR^2 + R^1OH$ carboxylic acid ester alcohol product ester product alcohol The process according to the invention can be applied to any transesterification reaction wherein the product alcohol formed in the reaction has a density greater than the product ester formed in the transesterification reaction. For example, if a triglyceride containing lauric, myristic and oleic acid residues is transesterified with methanol, glycerine, the alcohol formed in the reaction, has a density greater than methyl laurate, methyl myristate or methyl oleate. In another example, if ethylene glycol diacetate is transesterified with methanol, ethylene glycol, the alcohol formed in the reaction, has a density greater than methyl acetate.

The process according to the invention is carried out by first reacting a carboxylic acid ester with an alcohol and an effective amount of a transesterification catalyst in a reaction zone to form a reaction mixture comprised of a product ester and a product alcohol. The carboxylic acid ester can be any ester of a monool or polyol such as ethylene glycol or glycerine. The mole ratio of alcohol to ester can be any ratio that is effective in converting substantially all of the carboxylic acid ester to product ester in a desired time period. Typically, the mole ratio will be about 3:1, preferably 6:1, and most preferably 8:1. An effective amount of catalyst is any amount necessary to convert substantially all of the carboxylic acid ester to product ester in a desired time period. Typically, the effective amount will vary from about 0.01 wt % to about 5 wt %, preferably 0.01–2 wt % and, most preferably 0.03–1.5 wt %. The catalyst can be any transesterification catalyst known to those skilled in the art. Typically, the catalyst will be a metal alkoxide, such as the metal alkoxide of the reactant alcohol. If, for example, the reactant alcohol is methanol then the catalyst might be a metal methoxide such as sodium or potassium.

The reaction zone can be any type of vessel commonly used for transesterification reactions examples of which include, but are not limited to, a reaction vessel having a stirrer or agitator, a vessel having a recirculation loop, or a static mixer within a pipe or a similar container. The reaction mixture is held in the reaction zone for a period of time sufficient to convert substantially all the carboxylic acid ester into product ester. The reaction mixture is then passed through a centrifugal separation zone which can be any type of separation apparatus that uses a centrifuge to separate liquids having different densities. Centrifugation allows for faster removal of the product alcohol from the transesterification reaction which assists in driving the reaction to completion. It is preferred that the centrifugal separation zone be comprised of a centrifugal separator. The preferred centrifugal separator is model V02, available from Costner Industries Nevada Corp. (CINC), and is described in U.S. Pat. No. 5,762,800, the entire contents of which are incorporated herein by reference.

In a particularly preferred embodiment, the process according to the invention is used to manufacture methyl esters of fatty acids via transesterification of triglycerides with methanol. The conversion of triglycerides to alkyl esters via transesterification with an alcohol and a metal alkoxide, preferably methyl esters via transesterification with methanol and sodium methoxide is well known. Current technology uses both batch and continuous processes for making methyl esters from triglycerides. In commercial scale batch processing, the triglyceride, methanol and sodium methoxide are added together in a stirred tank reactor and reacted at 75–80° C. for a period of time, usually about one hour. The agitator is then turned off and the mixture is allowed to settle. The glycerine layer will be on the bottom and is drained from the vessel. The agitator is then turned on, additional sodium methoxide is added and the mixture is reacted for another hour at 75–80° C., glycerine drained, the crude methyl ester is water washed and dried. In a continuous process, the triglyceride, methanol and catalysts are metered together using pumps and mixing is accomplished by pumping the mixture through a static mixer and long lengths of piping to a settling tank In this tank, the mixture is pumped in on one side of the tank, the methyl esters are removed on the other side and the glycerine is drained from the bottom. Once the methyl esters leave this settling tank, they are further mixed with additional methanol and catalyst, pumped through a static mixer, pushed through piping and into a second settling tank. The methyl esters are pumped from this tank and further refined.

The process according to the present invention can employ any type of triglyceride including, but not limited to, coconut oil, palm kernel oil, sunflower oil, canola oil, soybean oil, safflower oil and beef tallow.

The mole ratio of methanol to triglyceride can be any ratio that is effective in converting substantially all of the triglyceride to product ester in a desired time period. Typically, the mole ratio of methanol to triglyceride will about 3:1, preferably 6:1, and most preferably 8:1. The preferred catalyst is a metal methoxide such as sodium or potassium methoxide. The amount can vary from about 0.01 wt % to about 5 wt %, preferably from about 0.01 to about 2 wt % and, most preferably from about 0.03 to about 1.5 wt %.

The triglycerides are introduced into a suitable reaction vessel having a means for mixing the reactants together such as agitator or a recirculation pump and having a means for the introduction of an inert gas such as $N_2$ or $CO_2$ to prevent darkening and oxidation of the final product. The triglycerides in the vessel are heated to 50–90° C., preferably to 70–85° C., and most preferably to 75–80° C. If a recirculation pump is used, it should be sized to provide material turnover rates between 1 and 20, preferably 2–15, and most preferably 3–10 times per hour. Once the triglycerides are heated to 75° C., dry methanol plus the catalysts are added to the vessel. The methanol mole ratio to the triglycerides is 3:1, preferred, 6:1, most preferred 8:1. Catalysts amount can vary from 0.01 wt % to 5 wt %, preferred 0.01–2 wt %, most preferred 0.03–1.5 wt %. The catalyst can be a metal alkoxide, preferably a metal methoxide such as potassium methoxide, and most preferrably sodium methoxide. They can be added through the charging hatch, preferred, added sub surface, most preferred, pumped into the vessel subsurface. The reaction is allowed to heat back up to 60–85° C., preferred 70–80° C., most preferred 75–80° C. Once the temperature reaches 75–80° C., the contents of the reactor are fed to a centrifugal separator, one example of which is described in U.S. Pat. No. 5,762,800, the entire contents of which are incorporated herein by reference.

The process according to the invention can be carried out as a batch or a continuous process. The process according to the invention can be modified if less than substantially all of the carboxylic acid ester is converted to product ester in step (1) of the process as described herein. In such an instance, the product ester stream from the centrifugal separator is recycled to the transesterification reaction zone after a first pass through the centrifugal separator one or more times until the desired product purity is obtained.

The process according to the invention can also be carried out by passing the alkyl ester from step (2) through a second centrifugal separation zone wherein the alkyl ester is contacted with water to remove residual glycerine and other impurities.

The following example is meant to illustrate but not to limit the invention.

EXAMPLE 1

Methyl soyate was prepared via transesterification with sodium methoxide and methanol. A 2-liter water-jacketed reactor fitted with a thermometer, nitrogen subsurface line water condenser and no agitator. Approximately 1.17 moles or 1000 grams of soybean oil, salad grade was charged to the reactor. The water was turned on the condenser and the bottom valve of the reactor was opened and the recirculation pump started. The water bath was set at 90° C. and was turned on. When the temperature of the oil reached 75° C., 225 grams of methanol which represents a 6 mole excess was added along with 0.08 wt % of sodium methoxide (25% solution in methanol) was added to the reactor. The reactor was made of glass so the oil phase and the methanol were present as two layers initially. After 5 minutes, the mixture became homogeneous, so the discharge line from the pump was switched to the inlet of a centrifugal separator, model V02, Costner Industries Nevada Corp. The centrifugal separator was turned on at 2000 RPM or 33.5 Hz. The heavy phase discharge line was set to empty into a beaker; the light phase outlet line from the centrifugal separator was set to return to the top of the reactor. After twenty minutes from the time the methanol and catalysts were added, an additional 0.07 wt % of sodium methoxide was added. Glycerine was discharged into the beaker 5 minutes after the centrifugal separator was first turned on. After 45 minutes from the initial methanol catalyst add or 25 minutes after the second catalyst add, the centrifugal separator and pump were shut down. The centrifugal separator was drained and combined with the amount collected from the discharge line of the centrifugal separator. By gas chromatography, the analysis of the crude methyl ester was 98.5% methyl ester, 1.2% monoglycerides and 0.3% diglycerides.

What is claimed is:

1. A process for making an alkyl ester of a carboxylic acid via transesterification comprising the steps of: (1) reacting a carboxylic acid ester with an alcohol and an effective amount of a transesterification catalyst in a reaction zone to form a reaction mixture comprised of a product ester and a product alcohol; (2) passing the reaction mixture from step (1) through a centrifugal separation zone wherein the second alcohol is separated from the second ester.

2. The process of claim 1 wherein the carboxylic acid ester is a triglyceride.

3. The process of claim 1 wherein the alcohol is methanol.

4. The process of claim 1 wherein the catalyst is sodium methoxide.

5. A process for making an alkyl ester of a carboxylic acid comprising the steps of: (1) reacting a triglyceryl ester of a carboxylic acid with an alcohol and an effective amount of a transesterification catalyst in a reaction zone to form a reaction mixture comprised of alkyl ester, glycerine and unreacted triglyceryl ester; (2) passing the reaction mixture from step (1) to a centrifugal separation zone to form a heavy glycerine phase and a light phase wherein the glycerine phase is continuously separated from the reaction mixture; (3) recycling the light phase to step (1).

6. The process of claim 5 wherein triglyceryl ester is selected from the group consisting of coconut oil, palm kernel oil, sunflower oil, canola oil, soybean oil, safflower oil and beef tallow.

7. The process of claim 5 wherein the alcohol is methanol.

8. The process of claim 5 wherein the catalyst is sodium methoxide.

9. A process for making an alkyl ester of a carboxylic acid comprising the steps of: (1) reacting a triglyceryl ester of a carboxylic acid with an alcohol and an effective amount of a transesterification catalyst in a reaction zone to form a reaction mixture comprised of alkyl ester and glycerine; (2) passing the reaction mixture from step (1) to a centrifugal separation zone wherein the glycerine is separated from the alkyl ester; (3) passing the alkyl ester from step (2) through a second centrifugal separation zone wherein the alkyl ester is contacted with water to remove residual glycerine and other impurities.

10. The process of claim 9 wherein the alcohol is methanol.

11. The process of claim 9 wherein the catalyst is sodium methoxide.

12. The process of claim 9 wherein the triglyceride is soybean oil.

* * * * *